(12) United States Patent
Edie et al.

(10) Patent No.: US 8,579,979 B2
(45) Date of Patent: Nov. 12, 2013

(54) EXPANDABLE INTERVERTEBRAL SPACERS AND METHODS OF USE

(75) Inventors: Jason A. Edie, Memphis, TN (US);
Lloyd Guyton Bowers Cooper, Birmingham, AL (US); John Caleb Dawson, Chicago, IL (US); Don Byron Walker, II, Muscle Shoals, AL (US); Jerrod Bradley Windham, Auburn, AL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/562,550

(22) Filed: Jul. 31, 2012

(65) Prior Publication Data

US 2012/0296430 A1    Nov. 22, 2012

Related U.S. Application Data

(63) Continuation of application No. 12/722,311, filed on Mar. 11, 2010, now Pat. No. 8,257,442, and a continuation of application No. 11/415,042, filed on May 1, 2006, now Pat. No. 7,708,779.

(51) Int. Cl.
*A61F 2/44*         (2006.01)
(52) U.S. Cl.
USPC ................ 623/17.15; 623/17.11; 623/17.16
(58) Field of Classification Search
USPC ........................................... 623/17.11–17.16
See application file for complete search history.

(56) References Cited

U.S. PATENT DOCUMENTS

| | | | |
|---|---|---|---|
| 196,117 A * | 10/1877 | Greenleaf ................ 254/103 |
| 4,553,273 A | 11/1985 | Wu | |
| 4,554,914 A | 11/1985 | Kapp et al. | |
| 4,657,550 A | 4/1987 | Daher | |
| 4,820,305 A | 4/1989 | Harms et al. | |
| 4,932,975 A | 6/1990 | Main et al. | |
| 5,002,576 A | 3/1991 | Fuhrmann et al. | |
| 5,026,373 A | 6/1991 | Ray et al. | |
| 5,062,850 A | 11/1991 | MacMillian et al. | |
| 5,236,460 A | 8/1993 | Barber | |
| 5,336,223 A | 8/1994 | Rogers | |
| 5,360,430 A | 11/1994 | Lin | |
| 5,397,364 A | 3/1995 | Kozak et al. | |
| 5,480,442 A | 1/1996 | Bertagnoli | |
| 5,522,899 A | 6/1996 | Michelson | |
| 5,571,190 A | 11/1996 | Ulrich et al. | |
| 5,571,192 A | 11/1996 | Schönhöffer | |
| 5,658,335 A | 8/1997 | Allen | |
| 5,702,451 A | 12/1997 | Biedermann et al. | |
| 5,702,453 A | 12/1997 | Rabbe et al. | |
| 5,702,455 A | 12/1997 | Saggar | |
| 5,723,013 A | 3/1998 | Jeanson et al. | |
| 5,725,528 A | 3/1998 | Errico et al. | |

(Continued)

FOREIGN PATENT DOCUMENTS

| EP | 1 080 703 A2 | 8/2000 |
|---|---|---|
| EP | 1 188 424 A1 | 8/2001 |

(Continued)

*Primary Examiner* — Andrew Yang

(57) ABSTRACT

An intervertebral spacer is inserted between vertebral members in a compact configuration and expanded post-insertion to contact the adjacent vertebral members. The intervertebral spacer comprises a first member and a second member movable with respect to the first member between retracted and extended positions.

5 Claims, 7 Drawing Sheets

(56) References Cited

U.S. PATENT DOCUMENTS

| | | |
|---|---|---|
| 5,776,197 A | 7/1998 | Rabbe et al. |
| 5,776,198 A | 7/1998 | Rabbe et al. |
| 5,989,290 A | 11/1999 | Biedermann et al. |
| 6,015,436 A | 1/2000 | Schonhoffer |
| 6,086,613 A | 7/2000 | Camino et al. |
| 6,156,038 A | 12/2000 | Zucherman et al. |
| 6,176,881 B1 | 1/2001 | Schär et al. |
| 6,190,413 B1 | 2/2001 | Sutcliffe |
| 6,190,414 B1 | 2/2001 | Young et al. |
| 6,193,755 B1 | 2/2001 | Metz-Stavenhagen et al. |
| 6,193,756 B1 | 2/2001 | Studer et al. |
| 6,200,348 B1 | 3/2001 | Biedermann et al. |
| 6,296,665 B1 | 10/2001 | Strnad et al. |
| 6,299,644 B1 | 10/2001 | Vanderschot |
| 6,344,057 B1 | 2/2002 | Rabbe et al. |
| 6,352,556 B1 | 3/2002 | Kretschmer et al. |
| 6,375,681 B1 | 4/2002 | Truscott |
| 6,375,682 B1 | 4/2002 | Fleischmann et al. |
| 6,375,683 B1 | 4/2002 | Crozet et al. |
| 6,395,032 B1 | 5/2002 | Gauchet |
| 6,395,034 B1 | 5/2002 | Suddaby |
| 6,409,766 B1 | 6/2002 | Brett |
| 6,447,547 B1 | 9/2002 | Michelson |
| 6,454,806 B1 | 9/2002 | Cohen et al. |
| 6,520,991 B2 | 2/2003 | Huene |
| 6,524,341 B2 | 2/2003 | Läng et al. |
| 6,562,074 B2 | 5/2003 | Gerbec et al. |
| 6,610,090 B1 | 8/2003 | Böhm et al. |
| 6,616,695 B1 | 9/2003 | Crozet et al. |
| 6,645,249 B2 | 11/2003 | Ralph et al. |
| 6,648,917 B2 | 11/2003 | Gerbec et al. |
| 6,660,038 B2 | 12/2003 | Boyer, II et al. |
| 6,719,796 B2 | 4/2004 | Cohen et al. |
| 6,723,126 B1 | 4/2004 | Berry |
| 6,752,832 B2 | 6/2004 | Neumann |
| 6,758,862 B2 | 7/2004 | Berry et al. |
| 6,776,798 B2 | 8/2004 | Camino et al. |
| 6,783,547 B2 | 8/2004 | Castro |
| 6,793,678 B2 | 9/2004 | Hawkins |
| 6,808,538 B2 | 10/2004 | Paponneau |
| 6,835,207 B2 | 12/2004 | Zacouto et al. |
| 6,852,129 B2 | 2/2005 | Gerbec et al. |
| 6,863,673 B2 | 3/2005 | Gerbec et al. |
| 6,866,682 B1 | 3/2005 | An et al. |
| 6,893,465 B2 | 5/2005 | Huang |
| 6,902,579 B2 | 6/2005 | Harms et al. |
| 6,908,485 B2 | 6/2005 | Crozet et al. |
| 2003/0191531 A1 | 10/2003 | Berry et al. |
| 2003/0199980 A1 | 10/2003 | Siedler |
| 2004/0049271 A1 | 3/2004 | Biedermann et al. |
| 2004/0073314 A1 | 4/2004 | White et al. |
| 2004/0172129 A1 | 9/2004 | Schafer et al. |
| 2004/0181283 A1 | 9/2004 | Boyer, II et al. |
| 2004/0186569 A1 | 9/2004 | Berry |
| 2005/0004572 A1 | 1/2005 | Biedermann et al. |
| 2005/0060036 A1 | 3/2005 | Schultz et al. |
| 2005/0090898 A1 | 4/2005 | Berry et al. |
| 2005/0113921 A1 | 5/2005 | An et al. |
| 2005/0209698 A1 | 9/2005 | Gordon et al. |
| 2005/0273169 A1 | 12/2005 | Purcell |
| 2005/0283245 A1* | 12/2005 | Gordon et al. ............ 623/17.15 |

FOREIGN PATENT DOCUMENTS

| | | |
|---|---|---|
| WO | WO 03/073964 A1 | 9/2003 |
| WO | WO 03/096937 A1 | 11/2003 |
| WO | WO 2004/026157 A2 | 4/2004 |
| WO | WO 2004/096103 A1 | 11/2004 |
| WO | WO 2004/100837 A1 | 11/2004 |
| WO | WO 2005/055887 A2 | 6/2005 |

* cited by examiner

EXPANDABLE INTERVERTEBRAL SPACERS AND METHODS OF USE

RELATED APPLICATIONS

The present application is a continuation of and claims priority from U.S. Utility patent application Ser. No. 12/722,311, filed on Mar. 11, 2010 now allowed, which claims priority from Utility patent application Ser. No. 11/415,042, filed on May 1, 2006, now U.S. Pat. No. 7,708,779, each of which are incorporated herein in their entirety by reference.

BACKGROUND

The present application is directed to devices and methods for stabilizing vertebral members, and more particularly, to intervertebral implants and methods of use for replacing an intervertebral disc, vertebral member, or combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion.

SUMMARY

The present application is directed to an intervertebral spacer with first and second members each with an outer side and an inner side. The members may be positioned in a stacked orientation with the inner sides facing together. A threaded extension may extend outward from the inner side of the first member. A cavity may be formed on the inner side of the second member, and may include a floor opposite from an open side. A ring gear may be positioned in the cavity and against the floor. The ring gear may include a threaded bore that receives the threaded extension and teeth that extend around an outer circumference. A gear may be positioned in the cavity and may include helical teeth that engage with the teeth on the ring gear. The gear may be rotatably positioned in the cavity with rotation in a first direction causing the first and second members to move apart and rotation in a second direction causing the first and second members to move together.

DETAILED DESCRIPTION

Figure 1:
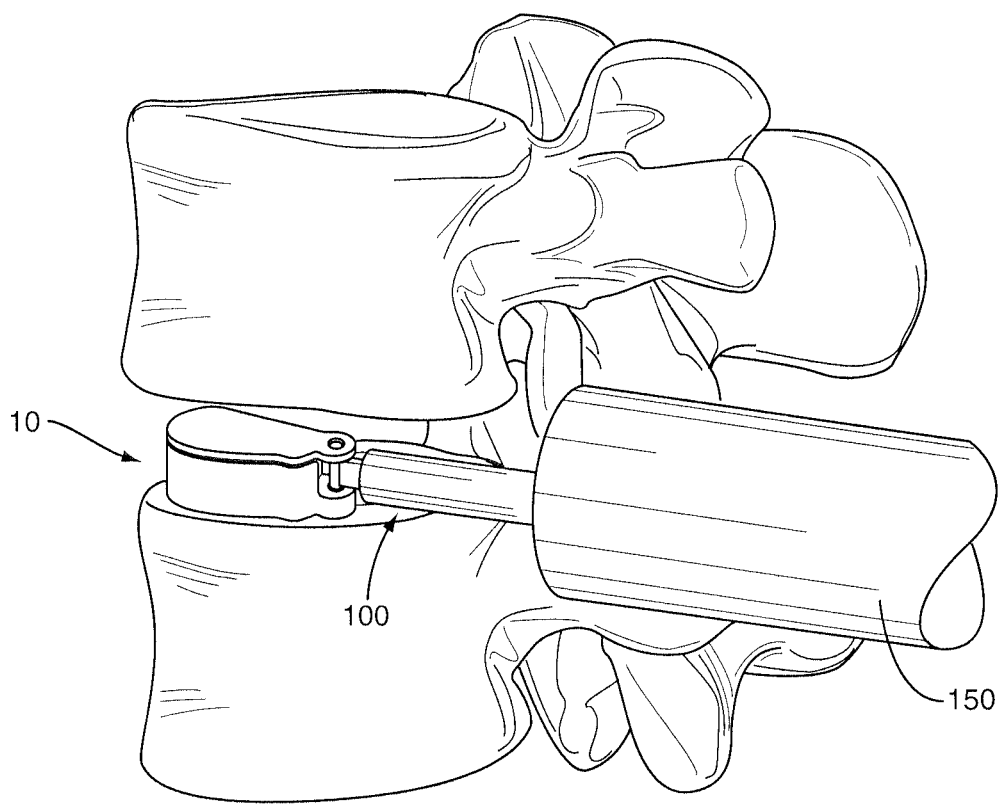
FIG. 1 is a perspective view of an exemplary intervertebral spacer in a retracted position.
Figure 2:
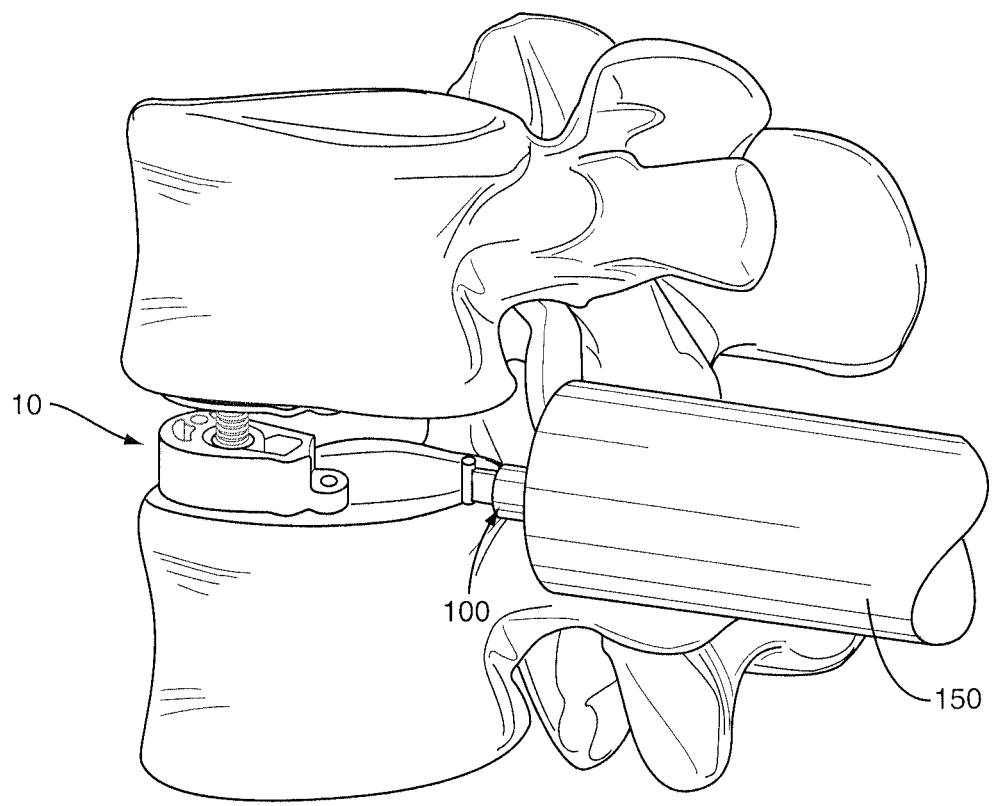
FIG. 2 is a perspective view of an exemplary intervertebral spacer in an extended position.
Figure 3:
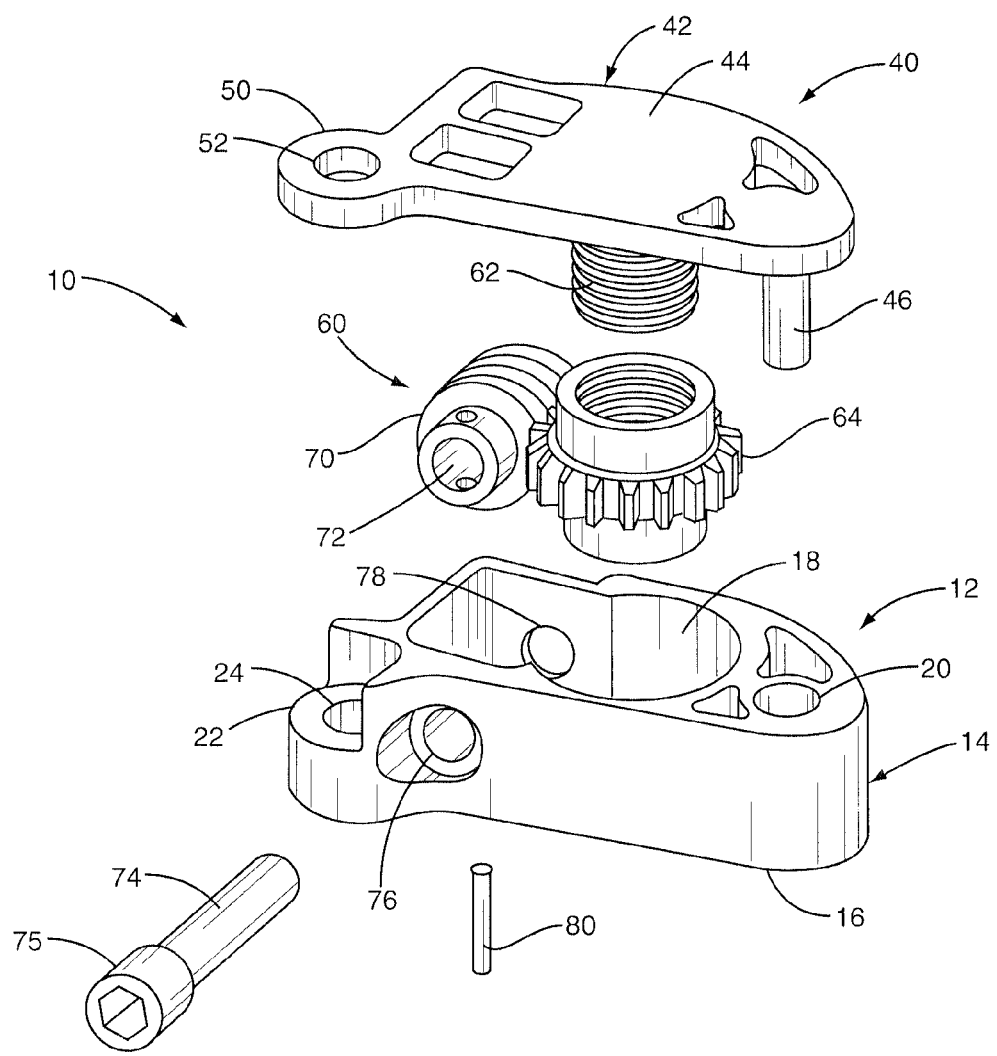
FIG. 3 is an exploded perspective view of an exemplary intervertebral spacer.

The present application relates to implants for replacing an intervertebral disc, vertebral member, or combination of both, and to methods of inserting the same. The implant comprises an intervertebral spacer 10 that can be inserted between vertebral bodies in a compact configuration as shown in FIG. 1 and subsequently expanded to contact the adjacent vertebral bodies as shown in FIG. 2.

FIGS. 3-6 illustrates one exemplary embodiment of the intervertebral spacer 10. The intervertebral spacer 10 comprises an inferior member 12 and a superior member 60 movable with respect to the inferior member 12 from a retracted position to an extended position. A jack mechanism 60 is interposed between the inferior member 12 and superior member 40 for moving the superior member 60 between the retracted and extended positions.

The inferior member 12 comprises a body 14 including a bottom surface 16 that contacts an adjacent vertebral body. The bottom surface 16 can be textured to grip the adjacent vertebral body. For example, small teeth, ridges, or grooves can be formed in the bottom surface 16 to improve gripping capability. The body 14 has a main cavity 18 formed therein to house components of the jack mechanism, and a guide hole 20 to receive a guide member 46 on the superior member. The body 14 further includes a shelf 22 having an opening 24 formed therein. The shelf 22 and opening 24 are configured to engage the head of an insertion tool 100 as will be hereinafter described in more detail.

Figure 5:
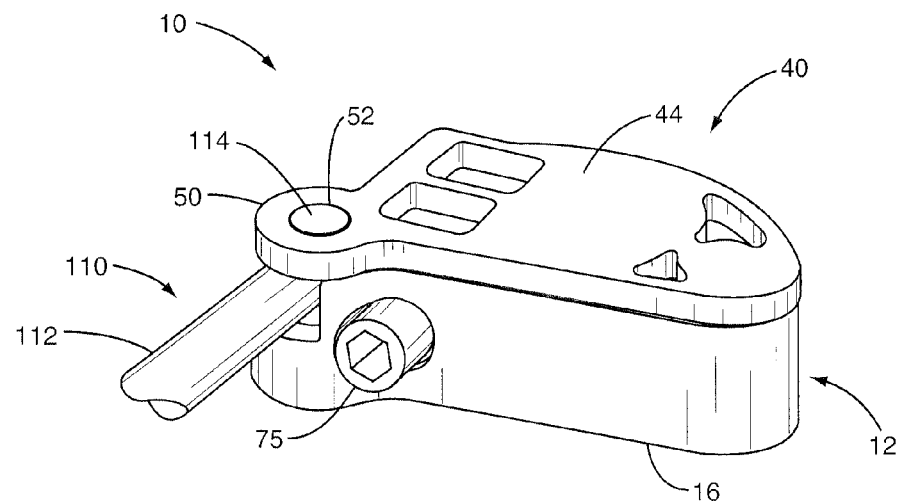
FIG. 5 is a perspective view of an exemplary intervertebral spacer in a retracted position.
Figure 7:
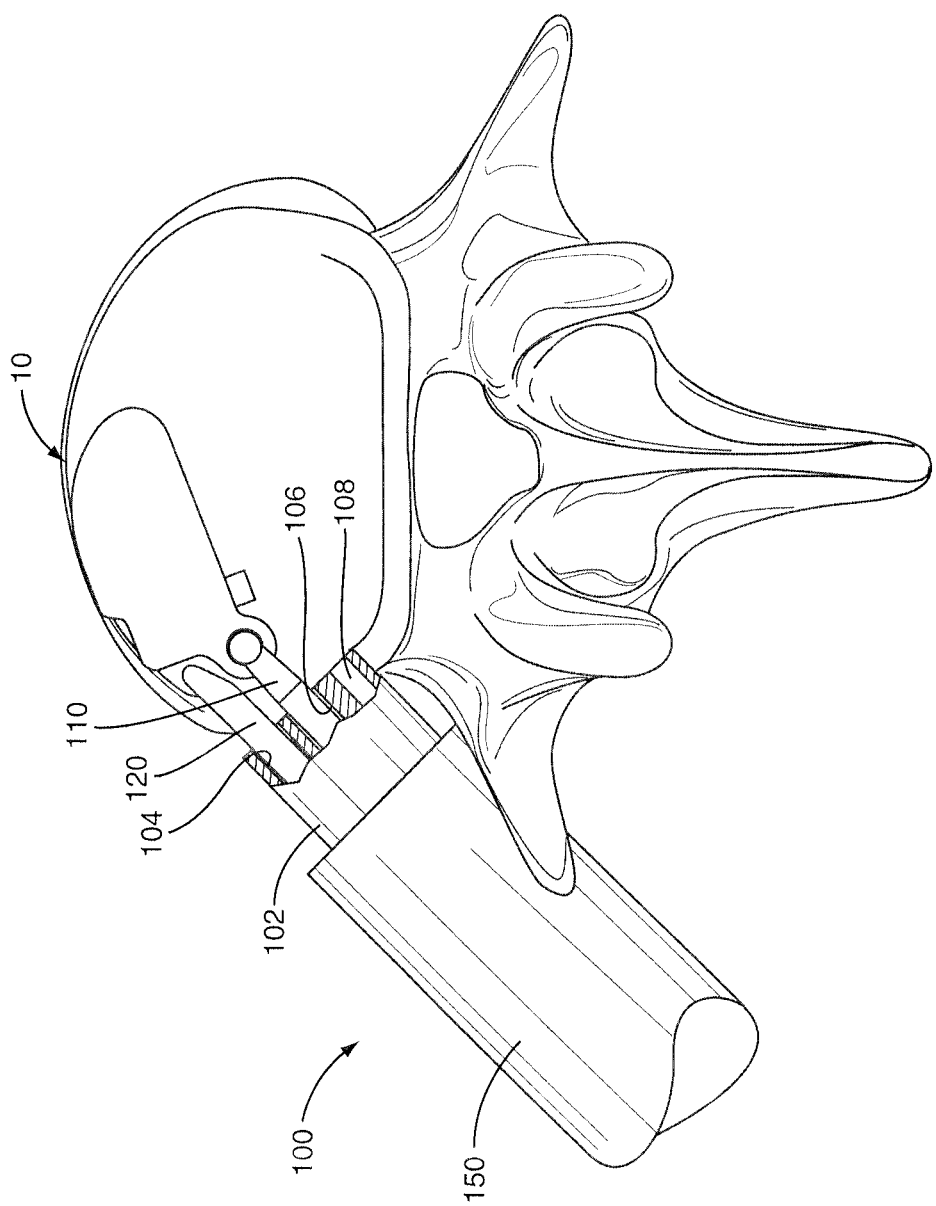
FIGS. 7 and 8 illustrate an exemplary method of inserting the intervertebral spacer.

The superior member 40, shown in FIGS. 5 and 7, comprises a plate 42 having a top surface 44 that engages an adjacent vertebral body. The top surface 44 can be textured to grip the vertebral body. For example, small teeth, ridges, or grooves can be formed in the top surface 44 to improve gripping capability. The top plate 42 is shaped to generally correspond to the shape of the inferior member 12. Guide member 46 extends downward from the top plate and fits within the guide hole in the inferior member 12. The top plate 42 further includes a tab 50 with an opening 52 formed therein to engage the insertion tool 100.

The jack mechanism 60 comprises a screw shaft 62 that extends downward from the bottom surface of the top plate 42, and a ring gear 64 that is rotatably mounted in the main cavity 18 of the inferior member 12. The ring gear 64 is internally threaded to mesh with the externally threaded screw shaft 62. When the ring gear 64 is rotated in a first direction, the superior member 40 is raised relative to the inferior member 12. Conversely, when the ring gear 64 is rotated in a second direction, the superior member 40 is moved toward the inferior member 12.

Figure 4:
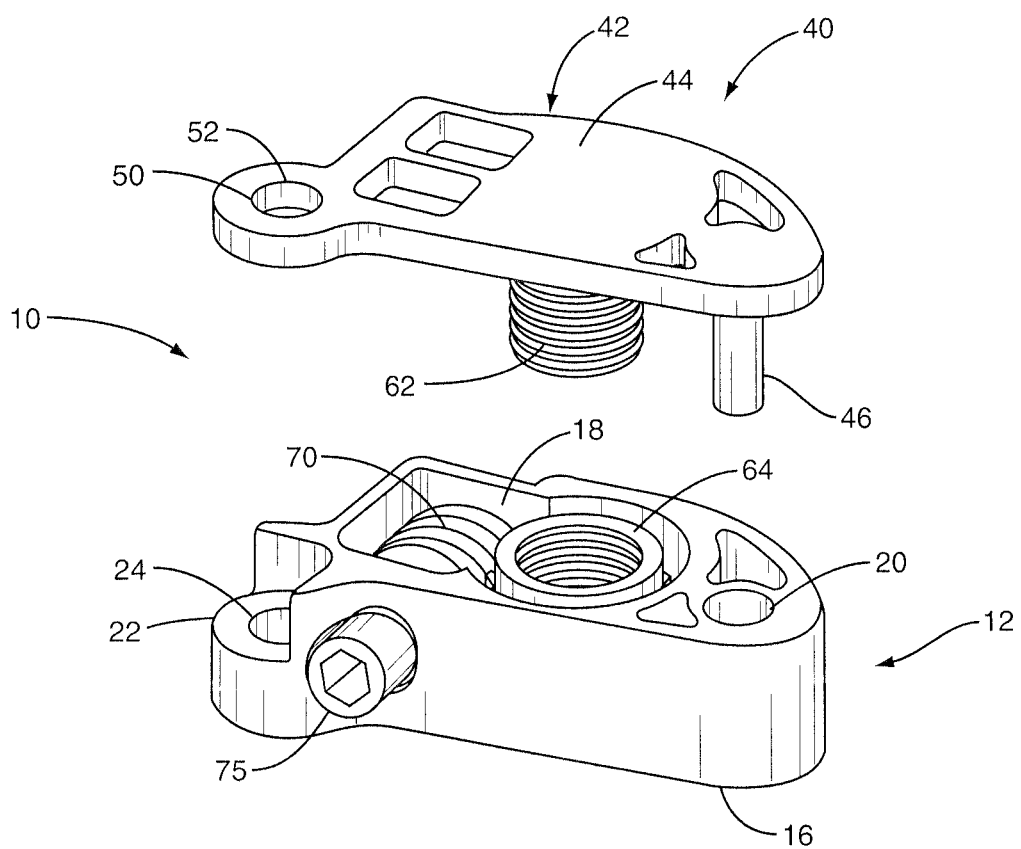
FIG. 4 is an exploded perspective view of an exemplary intervertebral spacer.

A drive gear 70 meshes with the ring gear 64. The drive gear is actuated by the surgeon to rotate the ring gear 64. In the exemplary embodiment, the drive gear comprises a worm gear with helical teeth that mesh with the teeth of the ring gear 64. The drive gear 70 has an axial bore 72 to receive a mounting shaft 74 which is rotatably journaled in openings 76, 78 in the main cavity 14 of the inferior member 12. The mounting shaft 74 includes a head 75 having a socket for receiving a tool. The drive gear 70 may be fixed to the mounting shaft 74 by any suitable means, such as pin 80. During assembly, the ring gear 64 and drive gear 70 are disposed within the main cavity 14 of the inferior member 12 as shown in FIG. 4. The axial bore 72 of the drive gear 70 is aligned with openings 76, 78 in the main cavity 14 of the inferior member 12. The mounting shaft 74 is inserted through the aligned openings in the wall of the main cavity 14 and through the axial bore of the drive gear 70. After the mounting shaft 74 is inserted, the drive gear 70 is secured to the mounting shaft 74, for example, by pin 80.

The inferior member 12 and superior member 40 can be made of any suitable material, such carbon reinforced PEEK. The bottom of the inferior member 12 and/or top plate 42 of the superior member 40 could be porous to allow the in-growth of bone. An embedded biologic coating, such as hydroxia appetite (HA), BMP, or calcium phosphate could be used to promote bone in-growth. The contact surfaces of the inferior and superior members 12 and 40 could also be textured to grip the adjacent vertebral bodies.

Figure 6:
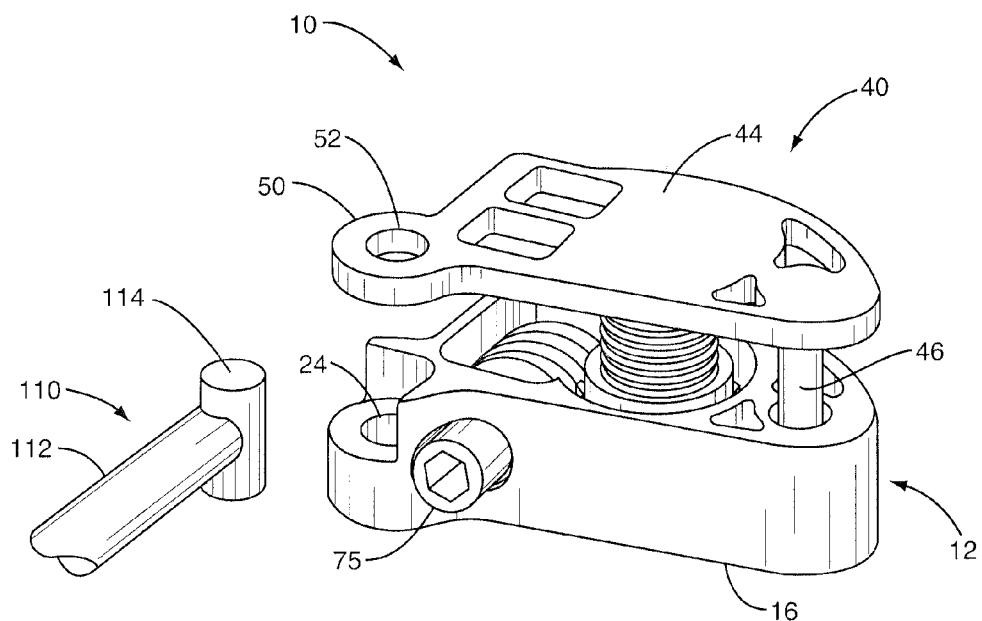
FIG. 6 is a perspective view of an exemplary intervertebral spacer in an expanded position.

In use, the superior member 40 is assembled to the inferior member 12 and placed in a compact configuration with the superior member 40 in a retracted position relative to the inferior member 12 as shown in FIG. 5. The intervertebral spacer 10, in a compact configuration, is inserted through a cannula 150 into an intervertebral space between two vertebral bodies. Those skilled in the art will appreciate that the intervertebral spacer 10 can be used to replace one or more discs and/or vertebral bodies. After the insertion of the intervertebral spacer 10, the drive gear 64 is rotated to cause the superior member 40 to extend away from the inferior member 12 as shown in FIG. 6. The superior member 40 is raised until the contact surfaces 16, 44 of the inferior and superior members 12 and 40 are engaged with the adjacent vertebral bodies. The gear teeth on the ring gear 64 and drive gear 70 are formed so as to lock at any selected height.

Figure 8:
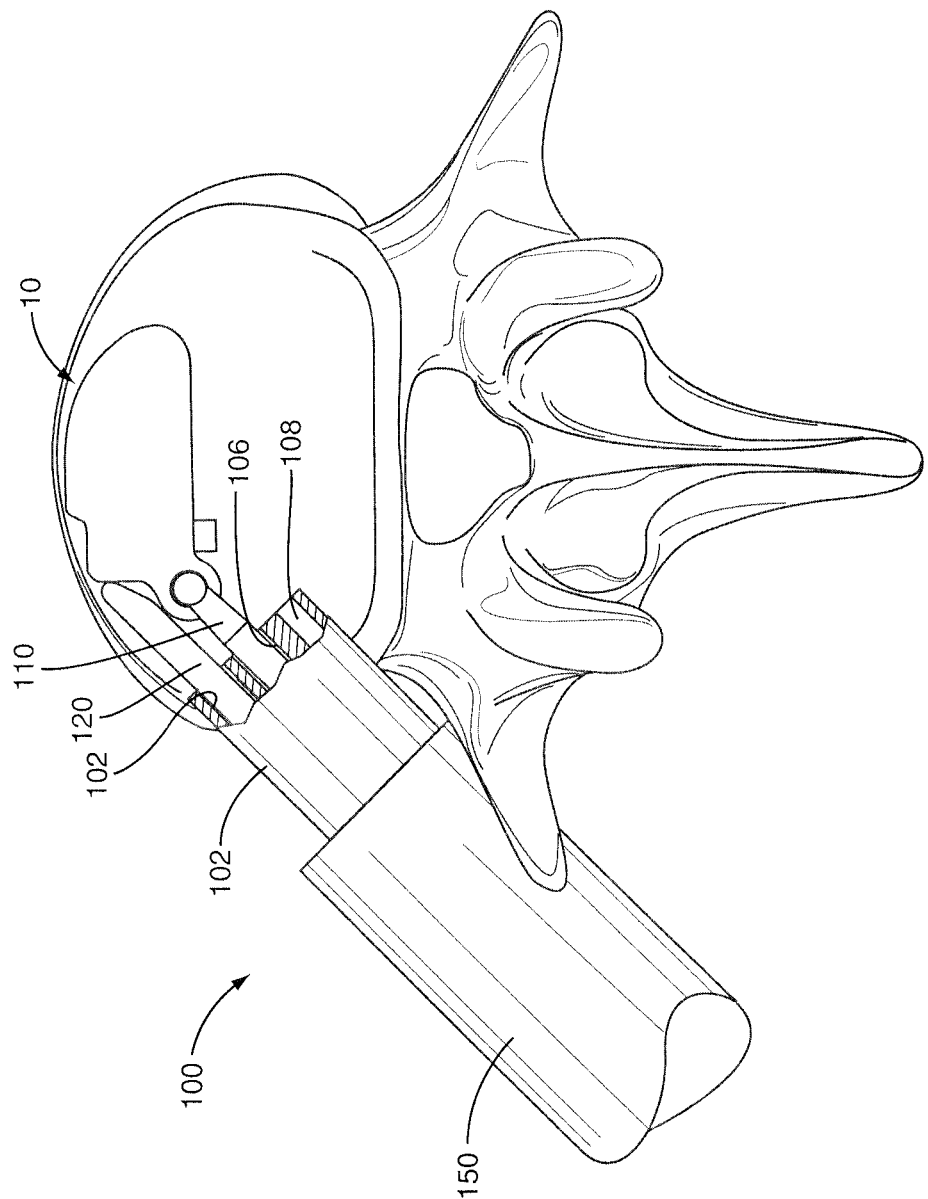

The intervertebral spacer 10 may be used in various regions of the spine, including the cervical, thoracic, lumbar and/or sacral portions of the spine. FIGS. 7 and 8 illustrate an exemplary insertion tool 100 that can be used to insert the intervertebral spacer 10. FIGS. 10 and 11 illustrate accessing the spine from a postero-lateral approach. Those skilled in the art will appreciate that other approaches may also be used, including posterior, anterior, antero-lateral and lateral approaches to the spine.

FIGS. 7 and 8 illustrate an exemplary insertion tool 100 to insert the intervertebral spacer 10. The insertion tool 100 includes an elongate housing 102 having three lumens 104, 106, and 108 formed therein, an engaging tool 110, and a push rod 120. Access to the intervertebral space is gained through a cannula 150 inserted into the body. FIGS. 7 and 8 illustrate the distal end of the cannula 150 and insertion tool 100. The engaging tool 110 includes an elongate shaft 112 that passes through the center lumen 106 in housing 102, and a cylindrical head 114 to engage the intervertebral spacer 10. As shown in FIG. 5, the cylindrical head 114 of the engaging tool 110 is configured to engage in openings 22, 52 on the inferior member 12 and superior member 40 respectively when the superior member 40 is moved to the retracted position. The intervertebral spacer 10 can rotate freely about the axis of the cylindrical head 104 during insertion to accurately position the intervertebral spacer 10. As the intervertebral spacer 10 is advanced through the cannula 150, the intervertebral spacer 10 initially assumes the position shown in FIG. 7. When the intervertebral spacer 10 exits from the end of the cannula 150, a push rod 104 inserted through lumen 104 in housing 102 is used to rotate the intervertebral spacer 10 into the proper angular position as shown in FIG. 8. A tool (not shown) can then be inserted through the lumen 108 to engage and rotate the mounting shaft 74. Rotation of the mounting shaft 74 causes the drive gear 64 to rotate, which in turn rotates the ring gear 64. Rotation of the ring gear 64 causes the screw shaft 62 to move axially upward raising the superior member 40 into contact with the superior vertebral body.

The embodiments described above include member 40 being a superior member and member 12 being inferior. In another embodiment, the orientation of these members 40, 12 may be interchanged with member 40 functioning as an inferior member and member 12 functioning as a superior member.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An intervertebral spacer comprising:
   an inferior member including a body having a bottom surface being configured to contact a vertebral body, the body defines a main cavity therein;
   a superior member including a plate having a top surface being configured to engage an adjacent vertebral body, the top surface including a guide member extending therefrom;
   a guide hole defined in the inferior member, the guide hole being configured to receive the guide member; and
   a jack mechanism disposed in the main cavity, wherein the jack mechanism is configured to cause the inferior and superior members to move in a first direction such that the inferior and superior members move apart and in a second direction such that the inferior and superior members move towards each other;
   wherein the jack mechanism includes a screw shaft extending from a bottom surface of the plate and a ring gear rotatably mounted in the main cavity, wherein the ring gear is internally threaded to mesh with the externally threaded screw shaft such that when the ring gear is rotated in a first direction, the superior member is raised relative to the inferior member and when the ring gear is rotated in a second direction, the superior member is moved toward the inferior member;

wherein a drive gear meshes with the ring gear, the drive gear being configured to rotate the ring gear;

wherein the drive gear includes an axial bore configured to receive a mounting shaft being rotatably journaled in the main cavity of the inferior member, the mounting shaft includes a head having a socket for receiving a tool.

2. The spacer of claim 1, wherein the top surface includes a shape substantially similar to a shape of the inferior member.

3. The spacer of claim 1, wherein the body further comprises a shelf having an opening configured to engage a head of an insertion tool.

4. The spacer of claim 1, wherein the top surface further includes a tab having an opening formed therein to engage an insertion tool.

5. The spacer of claim 1, wherein the drive gear includes a worm gear with helical teeth that are configured to mesh with teeth of the ring gear.

* * * * *